May 16, 1972 R. PAUL Plant Pat. 3,179
PEACH TREE
Filed Nov. 12, 1969
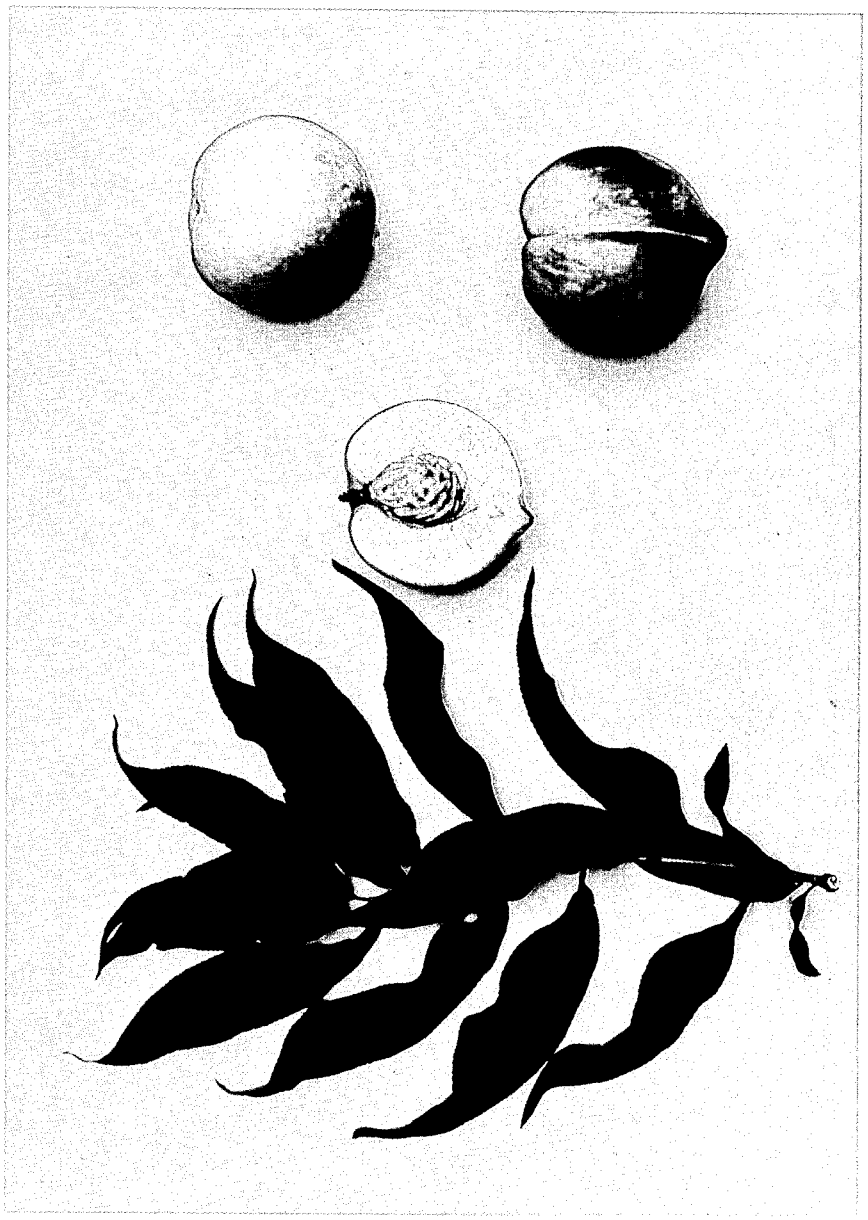
RONALD PAUL
INVENTOR
Virgil L. Gerard
ATTORNEY

United States Patent Office

Plant Pat. 3,179

Patented May 16, 1972

3,179

PEACH TREE

Ronald Paul, 5485 E. Heaton Ave., Fresno, Calif. 93727

Filed Nov. 12, 1969, Ser. No. 876,148

Int. Cl. A01h *5/03*

U.S. Cl. Plt.—43 1 Claim

The present invention relates to a peach tree and more particularly to a new and distinct variety thereof broadly characterized by its vigorous, regular bearing tree, and its early ripening fruit which is highly colored with red over half or more of its surface and has a distinct yellow color along the suture line, round shaped, relatively large for its season, and has very few split pits.

The instant variety most nearly resembles the Redhaven variety (unpatented) but is an improvement thereon in that it bears fruit which is ten to fourteen days earlier, more round in shape, and has a better color.

The instant variety most nearly resembles Vestal's variety but is an improvement thereon in that it ripens about ten days earlier—the instant variety being firm to eating soft ripe by June 6th and the Vestal variety being firm ripe with few eating ripe by June 16.

The present variety is distinctive from the Vestal and Sherrill (Plant Patents 1,716 and 2,102, respectively) in the following particulars.

The moderately productive tree of the instant variety has crenate leaves, 3 to 6 glands, and bears fruit which ripens unevenly—earliest at the apex and along both lips, is firm to eating soft ripe by June 6. The fruit is of variable shape, generally globose and has a marked suture depression beyond the pistil point and a pronounced mucronate apex. The Vestal variety is a productive tree having finely serrated leaves having 0 to 7 glands. Its fruit ripens evenly with the fruit firm ripe, and a few eating ripe, by June 16—ten days later than the instant variety. Its fruit is ovoid to near globose in shape and has a slight suture depression beyond the pistil point and a short, mucronate apex. The Sherrill variety is a very productive tree with finely serrated leaves bearing no stipules. Its fruit is uniform in shape, ripens evenly and has a distinct shallow suture extending from base to apex with the suture showing on only one side, whereas the instant variety has the suture showing on both sides.

The instant variety has moderate down which rolls up when rubbed. Vestal has some down, short and scant. Sherrill has moderate down which does not roll up when rubbed.

The flesh of the instant variety has abundant, coarse and medium tough fibers whereas Vestal has few, tender fibers.

The flavor of the instant variety has a delicate flavor. The Vestal variety has a vinous flavor.

The present variety has flesh which clings to the stone except when ripened off the tree, then some are clings and some are partly free. The Vestal stone is semi-free when firm ripe and free when soft ripe. The Sherrill stone clings.

The pits of the instant variety's stone are generally circular whereas those of the Sherrill variety are elongated.

These distinctions are columnized as follows:

| Characteristic | Instant variety | Vestal variety | Sherrill variety |
|---|---|---|---|
| Tree: | | | |
| Productivity | Moderate | Productive | Very productive. |
| Leaves: | | | |
| Margin | Crenate | Finely serrated | Finely serrated. |
| Glands | 3 to 6, average 4.4 | 0 to 7 | 3 to 5. |
| Stipules | On new leaves, falling off early | On new leaves, falling off early | None. |
| Fruit: | | | |
| Maturity | Firm to eating soft ripe, June 6, 1969 | Firm ripe, few eating, June 16,1957 | Firm ripe May 28, 1960. |
| Shape | Variable, generally globose | Ovoid to near globose | Uniform, symmetrical, globose. |
| Lips | Mostly unequal | Usually unequal | Equal. |
| Suture | Discontinues near apex, marked depression beyond pistil point. | Slight depression beyond pistil point | Distinct, shallow, from base to apex. |
| Cavity | Suture showing both sides | Suture both sides | Suture one side. |
| Base | Retuse | Retuse | Rounded. |
| Apex | Pronounced mucronate | Short, mucronate | Prolonged. |
| Skin: | | | |
| Tenacity | Tenacious to flesh | Tenacious except when soft | Free. |
| Down | Moderate, rolls up when rubbed | Some, scant and short | Moderate, does not roll up when rubbed. |
| Flesh: | | | |
| Fibers | Abundant, coarse, medium tough | Few, tender | |
| Ripens | Unevenly, earliest at apex and along both lips | Even | Even. |
| Flavor | Sub-acid, delicate | Sub-acid, vinous | Delicate. |
| Stone: | | | |
| Type | Cling, except when ripened off tree—then some cling and some partly free. | Semi-free when firm ripe, free when soft ripe | Cling. |
| Form | Obovate | Obovate | Globose. |
| Surface | Irregularly pitted and furrowed | Pitted throughout, irregularly furrowed | Regularly furrowed. |
| Pits | Generally circular | Usually circular | Elongated. |

I discovered the present variety on a farm owned by me at Fresno, Fresno County, Calif., as follows: Several years ago I noticed that one of the Redhaven variety (unpatented) peach trees in an orchard on my said farm had a different limb on it. The leaves and blossoms came on the limb at the same time or slightly earlier than on the other limbs, or the other trees in the orchard. Eventually, the limb budded and produced fruit which came on earlier than the fruit from other limbs on the tree or on other trees in the orchard. The fruit was substantially identical to the Redhaven peach except for its earlier maturity, more distinct yellow color along the suture line, and its size which varies from the same to larger.

Subsequently, I grafted June buds from the limb on other Redhaven trees. The grafts grew well and ultimately yielded fruit which had characteristics identical to the fruit from the original limb.

The accompanying drawing is a color photographic print of a characteristic whole fruit (two views) of the subject new variety showing the shape and skin color, a characteristic fruit divided at its suture plane showing the flesh color and pit, and a characteristic twig with leaves and glands.

Referring now more specifically to the pomological characteristics of this new and distinct variety of peach tree, the following has been observed under the ecological conditions prevailing near Fresno, Fresno County, Calif., and is an outline description thereof. All major color plate identifications are by reference to Maerz and Paul, Dictionary of Color, First Edition.

*Tree*

General: Medium size, medium vigorous, vase shaped when pruned, same as Redhaven.

Productivity: Sets fruit moderately but regularly, same as Redhaven.

Trunk: Medium size, shaggy gray, same as Redhaven.

Branches: Medium slender, gray on older branches and brown on younger branches, same as Redhaven.

Lenticels: Medium size, numerous, same as Redhaven.

Leaves: Location, from center portion of terminal shoots 30 to 36 inches long; medium size, 4 to 7 inches long, ¾ to 1½ inches wide; lanceolate; tip, acuminate; medium thick; width-length ratio 5 or 6 to 1; class (Meador & Blake: Proceedings of the American Society for Horticultural Science, volume 37, page 206) 2 and 3; margin crenate; glandular; petiole, medium size; glands reniform, located at base of leaf and on petiole, one to three to six average 4.4, stipules on young leaves, falling off early; color, upper surface dark green, lower surface light green, veins, very light yellowish green, otherwise generally same as Redhaven.

*Flower buds*

Medium size, plump, free, pubescent, same as Redhaven.

*Flowers*

Blooms: Same or slightly earlier than Redhaven, moderately abundant, pollen abundant, same as Redhaven.

Size: Small, same as Redhaven.

Color: Pink with salmon tinge, same as Redhaven.

*Fruit (described at maturity)*

Maturity: Firm to eating soft ripe, June 6, 1969.

Size: Variable diameter, axially 2¼ to 2¾, mostly 2⅝ inches transverse in suture plane 2⅜ to 3 inches, right angle to suture plane 2 9/16 to 2 7/16 inches, generally same as Redhaven.

Shape: Variable; generally globose on mature fruit; oval on immature fruit; compressed right angle to suture plane on very ripe fruit, same as Redhaven.

Suture: A distinct depression which extends from base to near apex but discontinues at apex and has marked depression beyond pistil point, lips mostly unequal, otherwise same as Redhaven.

Dorsal surface: Rounded, same as Redhaven.

Cavity: Medium abrupt; elongated in suture plane and showing on both sides; depth ¼ to ½ inch, breadth ½ to ¾ inch, length averages ¾ inch; yellow brown color with red blush when exposed to the sun; same as Redhaven.

Base: Otherwise retuse; same as Redhaven.

Apex: Pronounced mucronate; pistil point, apical, very short; same as Redhaven.

Stem: Medium size, about ⅛ inch in diameter, and ¼ inch long; adheres frequently to stone; same as Redhaven.

Skin: Medium thick, medium tough, sweet, tenacious to flesh; undercolor yellow 9–L–2 with red blush from light red 1–I–10 to darker red blush 6–L–6 with lighter red stripes 2–L–10 with deeper yellow 9–L–6 along suture; down, moderate, rolls up when rubbed; otherwise scant; generally same as Redhaven except for deeper yellow along suture.

Flesh: Color, very light yellow 9–K–2 near stone to light yellow 9–K–4 nearer skin; amygdalin, moderate; juice, moderate, rich; texture, generally meaty to melting when soft ripe; fibers, abundant in amount, course, medium tough, ripens unevenly, earliest at apex and along both lips; flavor, subacid delicate; firmness, when shipping ripe very firm, when soft ripe melting to slightly firmer near stone; good eating quality; otherwise substantially the same as Redhaven.

*Stone*

Generally: Clings to flesh execpt when fruit is ripened off of the tree, then flesh clings in some and in others is free in part from the stone; otherwise same as Redhaven.

Size: Medium to small, 1¼ to 1½ inches long, ⅞ to 1 inch wide, ⅝ to ¾ inch thick; same as Redhaven.

Form: Generally obovate, same as Redhaven.

Base: Straight to oblique; same as Redhaven.

Hilum: Oval; same as Redhaven.

Apex: Acuminate, some years more pronounced; same as Redhaven.

Surface: Irregularly pitted and furrowed, pits generally circular; same as Redhaven.

Ventral edge: Thick with many fine furrows and with deep groove on each side; same as Redhaven.

Dorsal edge: Deep groove extending from base half way more or less to apex; same as Redhaven.

Color: Light tan; same as Redhaven.

Tendency to split: Slight; same as Redhaven.

Use: Local and distant fresh markets, eating quality good; same as Redhaven.

Although my new variety of peach possesses the described characteristics under the growing conditions near Fresno, Fresno County, Calif. having first been observed there, it is to be understood that variations of the usual magnitude in characteristics incident to the growing conditions, fertilization, pruning and pest control are to be expected.

Having thus described and illustrated my new variety of peach tree, what is claimed is:

1. A new and distinct variety of peach substantially as illustrated and described, which is characterized by its early maturity, approximately two weeks earlier than the unpatented Redhaven and by fruit having the same general characteristics as the Redhaven but deep yellow skin color along the suture a more pronounced cling stone and a more pronounced mucronate apex.

References Cited

UNITED STATES PATENTS

| | | | |
|---|---|---|---|
| P.P. 1,716 | 6/1958 | Vestal | Plants—43 |
| P.P. 2,102 | 11/1961 | Sherrill | Plants—43 |

ROBERT E. BAGWILL, Primary Examiner